United States Patent [19]

Coates

[11] Patent Number: 4,514,568

[45] Date of Patent: Apr. 30, 1985

[54] 5-(4-NITROPHENYL)-2(1H)-PYRAZINONES

[75] Inventor: William J. Coates, Welwyn Garden City, England

[73] Assignee: Smith Kline & French Laboratories Limited, Welwyn Garden City, England

[21] Appl. No.: 500,484

[22] Filed: Jun. 2, 1983

[30] Foreign Application Priority Data

Jun. 5, 1982 [GB] United Kingdom ............... 8216437
Jan. 8, 1983 [GB] United Kingdom ............... 8300476

[51] Int. Cl.$^3$ ............................................ C07D 241/18
[52] U.S. Cl. .................................................. 544/408
[58] Field of Search ....................................... 544/408

[56] References Cited

U.S. PATENT DOCUMENTS 3,745,161  7/1973  Tsung-Ying et al. ............... 544/406

OTHER PUBLICATIONS

March, ed., *Advanced Organic Chem.*, 2nd ed., (1977), pp. 474–476.
Sheradsky et al., J.C.S. Perkin I:1296–1299, (1977).
Ohta et al., Hukusokan Kagaku Toronkai Kuen Yoshishu 8th:84–88, (1975), (Chem. Abstr. 84:164,723Y).

*Primary Examiner*—Mark L. Berch
*Assistant Examiner*—William A. Teoli, Jr.
*Attorney, Agent, or Firm*—Edward T. Lentz; Janice E. Williams; Alan D. Lourie

[57] ABSTRACT

This invention relates to 5-(phenyl)-2(1H)-pyrazinones substituted in the 4-position of the phenyl ring by a nitro group, and to a process for their preparation. These compounds are useful intermediates in the synthesis of inotropic compounds. One specific compound is 5-(4-nitrophenyl)-2(1H)-pyrazinone.

2 Claims, No Drawings

5-(4-NITROPHENYL)-2(1H)-PYRAZINONES

The present invention relates to pyrazinone derivatives and in particular to such compounds having a substituted phenyl group at the 5-position of the pyrazinone ring. The invention further relates to a process for their preparation and their use as intermediates in the synthesis of inotropic agents.

The compound 5-(4-aminophenyl)-2(1H)-pyrazinone has been disclosed in the *Journal of the Chemical Society*, Perkin I, 1977, page 1296, but no useful biological activity was suggested.

Accordingly the present invention provides a compound of the formula (I):

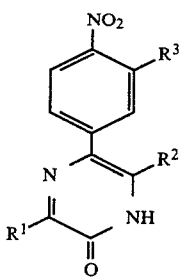

(I)

wherein $R^1$, $R^2$, and $R^3$ are independently hydrogen or $C_{1-4}$ alkyl.

Suitably $R^1$ is $C_{1-4}$ alkyl for example methyl, ethyl, n-propyl or iso-propyl. Preferably $R^1$ is hydrogen.

Suitably $R^2$ is $C_{1-4}$ alkyl for example methyl. Preferably $R^2$ is hydrogen.

Suitably $R^3$ is $C_{1-4}$ alkyl for example methyl, ethyl, n-propyl or iso-propyl. Preferably $R^3$ is hydrogen.

Thus in a preferred aspect of the compounds of the formula (I), $R^1$, $R^2$ and $R^3$ are simultaneously hydrogen.

The compounds of the formula (I) are useful intermediates in the preparation of compounds of the formula (II):

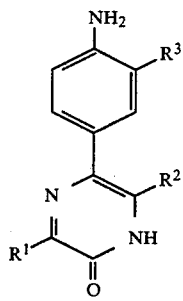

(II)

wherein $R^1$, $R^2$ and $R^3$ are as hereinbefore defined.

Suitably the reduction of a compound of the formula (I) to a compound of the formula (II) is performed via catalytic hydrogenation, either using hydrogen gas or via catalytic transfer hydrogenation, suitably in the presence of a base. Suitable catalysts include conventional transition metal catalysts for example Palladium on a conventional carrier, for example about 10% Palladium on Charcoal. The hydrogenation may be performed at non-extreme pressure, for example at atmospheric pressure or at pressures of up to 10 atmospheres ($10.13 \times 10^5$ Pa), preferably at about 3 atmospheres ($3 \times 10^5$ Pa). Suitably the base is in aqueous alcohol for example hydroxide in a $C_{1-4}$ alkanol for example ethanol. In an alternative aspect the reduction is performed with hydrazine as the hydrogen source in aqueous base in the presence of a conventional transition metal catalyst for example 10% Palladium on Charcoal preferably at an elevated temperature. In one aspect the aqueous base may be hydrazine, alternatively the aqueous base may be sodium hydroxide or the like.

The compounds of the formula (II) and salts thereof are used for the treatment of mammals including humans and are normally formulated in accordance with standard pharmaceutical practice as a pharmaceutical composition.

Compounds of formula (II) and their pharmaceutically acceptable salts may be administered orally, parenterally, trans-dermally or rectally.

Compounds of formula (II) and their pharmaceutically acceptable salts which are active when given orally can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet or capsule, any pharmaceutical carrier routinely used for preparing solid formulations may be used. Examples of such carriers include magnesium stearate, starch, lactose and sucrose.

Typical parenteral compositions consist of a solution or suspension of the compound or salt in a sterile aqueous carrier or parenterally acceptable oil, for example polyethylene glycol in saline.

A typical suppository formulation comprises a compound of formula (II) or a pharmaceutically acceptable salt thereof which is active when administered in this way, with a binding and/or lubricating agent for example gelatin or cocoa-butter or other low melting vegetable waxes or fats.

Preferably the composition is in unit dosage form for example a tablet or capsule so that the patient may administer to himself a single dose.

Each dosage unit contains preferably from 15 to 250 mg of a compound of formula (II) or a pharmaceutically acceptable salt thereof calculated as the pyrazinone.

The daily dosage regimen for a mammal is from about 0.25 mg/Kg to about 25 mg/Kg of the compound of formula (II) or a pharmaceutically acceptable salt thereof calculated as the free pyrazinone moiety. The active ingredient may be administered from 1 to 6 times a day, sufficient to increase cardiac output. The compositions have positive inotropic activity and vasodilator activity and are of use in the treatment of cardiovascular diseases which can be treated by compounds having either or both of these activities. One such disease condition is congestive heart failure.

In another aspect of this invention there is provided a process for the preparation of a compound of the formula (I) which comprises the nitration of a compound of the formula (III):

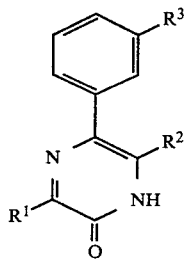

(III)

wherein R¹, R² and R³ are as hereinbefore defined.

Suitably the nitration of the compounds of the formula (III) is preformed at low temperatures for example below 5° C. and more suitably between −5° C. and −25° C., for example at about −15° C. We have found a mixture of fuming nitric acid and sulphuric acid to be an effective nitrating agent, preferably in a ratio of between 4:1 to 8:1 (vol/vol), for example about 6:1. We have found that at ambient temperatures and at elevated temperatures (for example 50° C.) that a number of undesired reactions occur; that is to say the pyrazinone ring can cleave, and nitration can preferentially occur on the pyrazinone ring particularly when R¹ is hydrogen giving rise to undesirable mono- and di-nitration products. It has been reported (Chem. Abs. 84: 164723y) that the nitration of a compound of the formula (III) wherein R¹, R² and R³ and simultaneously hydrogen gives rise to a compound wherein a nitro group replaces R¹. This was unambigously proved by an alternative synthesis. Thus it is unexpected that compounds of the formula (I) are prepared in high yields (about 80%) by the nitration of compounds of the formula (III).

The compounds of the formula (III) are prepared by known methods.

EXAMPLE 1

5-phenyl-2-(1-H)-pyrazinone (5 g) was added in portions during 30 minutes to a stirred mixture of fuming nitric acid (30 ml) and sulphuric acid (5 ml) at −5° C. The mixture was stirred in the cold for 30 minutes, and the temperature of the mixture was then allowed to rise to 10° C. The mixture was then poured into ice-water (250 ml) to give 5-(4-nitrophenyl)-2-(1H)-pyrazinone recrystallised from dimethylformamide, m.p. 336°–338° C., δ (DMSO-d₆) 8.15 and 8.30 (2d, 3-and 6- protons of pyrazinone ring), 8.18 (m, phenyl); ν max (Nujol mull) 3200–2500 (NH), 1690, 1675, 1545, 1510, 1349, 860 and 750 cm⁻¹.

EXAMPLE 2

5-Phenyl-2-(1H)-pyrazinone (56 g) was added in portions over 30 minutes to a stirred mixture of concentrated sulphuric acid (35 ml) and fuming nitric acid (200 ml). The temperature of the nitrating mixture was initially at −20° C. and care was taken to ensure that the temperature did not rise above −15° C. When the pyrazinone had completely dissolved the reaction mixture was allowed to warm to −10° C., stirred for a further 30 minutes, and poured slowly on to ice/water (1500 ml). A pale yellow solid precipitated which was collected by filtration, washed with a small amount of cold water and dried to afford 5-(4-nitrophenyl)-2-(1H)-pyrazinone (58.1 g).

DESCRIPTION 1

5-(4-Nitrophenyl)-2-(1H)-pyrazinone (0.1 g) was hydrogenated over 10% Palladium on Charcoal (0.01 g) at atmospheric pressure in 50% aqueous dimethylformamide containing 2N sodium hydroxide (0.46 ml). Once the theoretical quantity of hydrogen uptake had been observed, the reaction mixture was filtered and the filtrate treated with HCl to pH 6 and evaporated. Trituration of the residue with water afforded 5-(4-aminophenyl)-2(1H)-pyrazinone (0.07 g), m.p. 269°–271.5° C. (with decomposition).

DESCRIPTION 2

5-(4-Nitrophenyl)-2-(1H)-pyrazinone (4.0 g) in powder form was slurried with sodium hydroxide solution (1.47 g) in water (20 ml) and ethanol (20 ml) at room temperature. The resultant brown mixture was stirred for one hour. To this mixture were added 10% Palladium on carbon (0.4 g) slurried in water (2 ml), followed by water (8 ml) and ethanol (10 ml). The resultant mixture was hydrogenated at 3.25×10⁵ Pa (45 p.s.i.) in a small Parr vessel for 30 minutes. When theoretical uptake of hydrogen had been observed, the catalyst was filtered through diatomaceous earth with water washing. The filtrate was refiltered, acidified with acetic acid to pH 4.5 and the resultant 5-(4-aminophenyl)-2-(1H)-pyrazinone (2.9 g) was collected by filtration and dried.

DESCRIPTION 3

5-(4-Nitrophenyl)-2-(1H)-pyrazinone (0.1 g) was warmed with hydrazine hydrate (1 ml) in 50% aqueous ethanol (2.5 ml). Water (about 3 ml) was added sufficient to provide a clear solution. The mixture was allowed to cool slightly and 10% Palladium on charcoal (0.01 g) added as a slurry in a small amount of water. The well-stirred mixture was re-heated for 2-minutes, stirred without heating for 2 minutes, cooled and filtered. The filtrate was evaporated under reduced pressure to give a residue which was suspended in a little water. Dilute hydrochloric acid was added to pH 6; the pale yellow solid was collected and washed with water to afford 5-(4-aminophenyl)-2(1H)-pyrazinone (0.06 g).

DESCRIPTION 4

5-(4-Nitrophenyl)-2(1H)-pyrazinone (0.1 g) was warmed with water (2.5 ml) and 1N sodium hydroxide solution (0.46 ml) to about 70° C. To this solution was added 10% Palladium on charcoal (0.01 g), and subsequently hydrazine hydrate (0.1 ml). The well-stirred mixture was heated for 2 minutes, stirred for a further 2 minutes and filtered whilst hot. The filtrate was taken to pH 6 with dilute hydrochloric acid, whereupon the solid was collected by filtration, washed with water and dried to give 5-(4-aminophenyl)-2(1H)-pyrazinone (0.07 g).

DESCRIPTION 5

In an adaptation of the process of Description 4 the filtrate was taken to pH 1-2 with dilute hydrochloric acid. To this well-stirred solution at room temperature was added sodium acetate thihydrate (1.2 g) and acetic anhydride (1 ml). The resultant mixture was stirred for 50 minutes at room temperature, the solid collected, washed with water and dried to give 5-(4-acetamidophenyl)-2(1H)-pyrazinone in 79% yield.

What we claim is:

1. A compound of the formula (I):

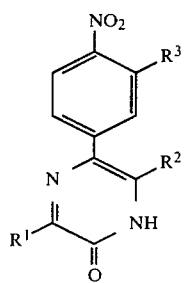
(I)
wherein $R^1$, $R^2$ and $R^3$ are independently hydrogen or $C_{1-4}$ alkyl.
2. A compound according to claim 1 wherein $R^1$, $R^2$ and $R^3$ are simultaneously hydrogen.
* * * * *